United States Patent [19]

Pignattini

[11] Patent Number: 5,006,067
[45] Date of Patent: Apr. 9, 1991

[54] DRIP PREVENTING DEVICE FOR DENTAL INSTRUMENTS

[75] Inventor: Giorgio Pignattini, Bologna, Italy

[73] Assignee: Castellini, S.p.A., Bologna, Italy

[21] Appl. No.: 303,466

[22] Filed: Jan. 27, 1989

[30] Foreign Application Priority Data

Feb. 9, 1988 [IT] Italy .................. 3330 A/88

[51] Int. Cl.⁵ .............................. A61C 1/02
[52] U.S. Cl. ...................... 433/98; 222/571; 433/84
[58] Field of Search .......... 433/28, 27, 80, 84, 433/85, 88, 98, 99, 100; 137/510, 312; 251/331; 222/571; 141/116

[56] References Cited

U.S. PATENT DOCUMENTS

| | | | |
|---|---|---|---|
| 3,895,748 | 7/1975 | Klingenberg | 222/571 |
| 3,961,640 | 6/1976 | Baker | 433/98 |
| 4,149,315 | 4/1979 | Page, Jr. et al. | 222/571 |
| 4,443,195 | 4/1984 | Matsui | 433/84 |
| 4,678,107 | 7/1987 | Ennis, III | 222/571 |
| 4,797,098 | 1/1989 | Kawata | 222/571 |

*Primary Examiner*—Cary E. Stone
*Attorney, Agent, or Firm*—Laff, Whitesel, Conte & Saret

[57] ABSTRACT

The device makes use of at least one plenum for each instrument, connected to the water circuit immediately upstream of the relative handpiece. Best results are obtained by connecting two such plenums to the water circuit in parallel, the one charged by the spray air circuit, the other by the power air circuit, as independent operation ensures greater reliability.

6 Claims, 6 Drawing Sheets

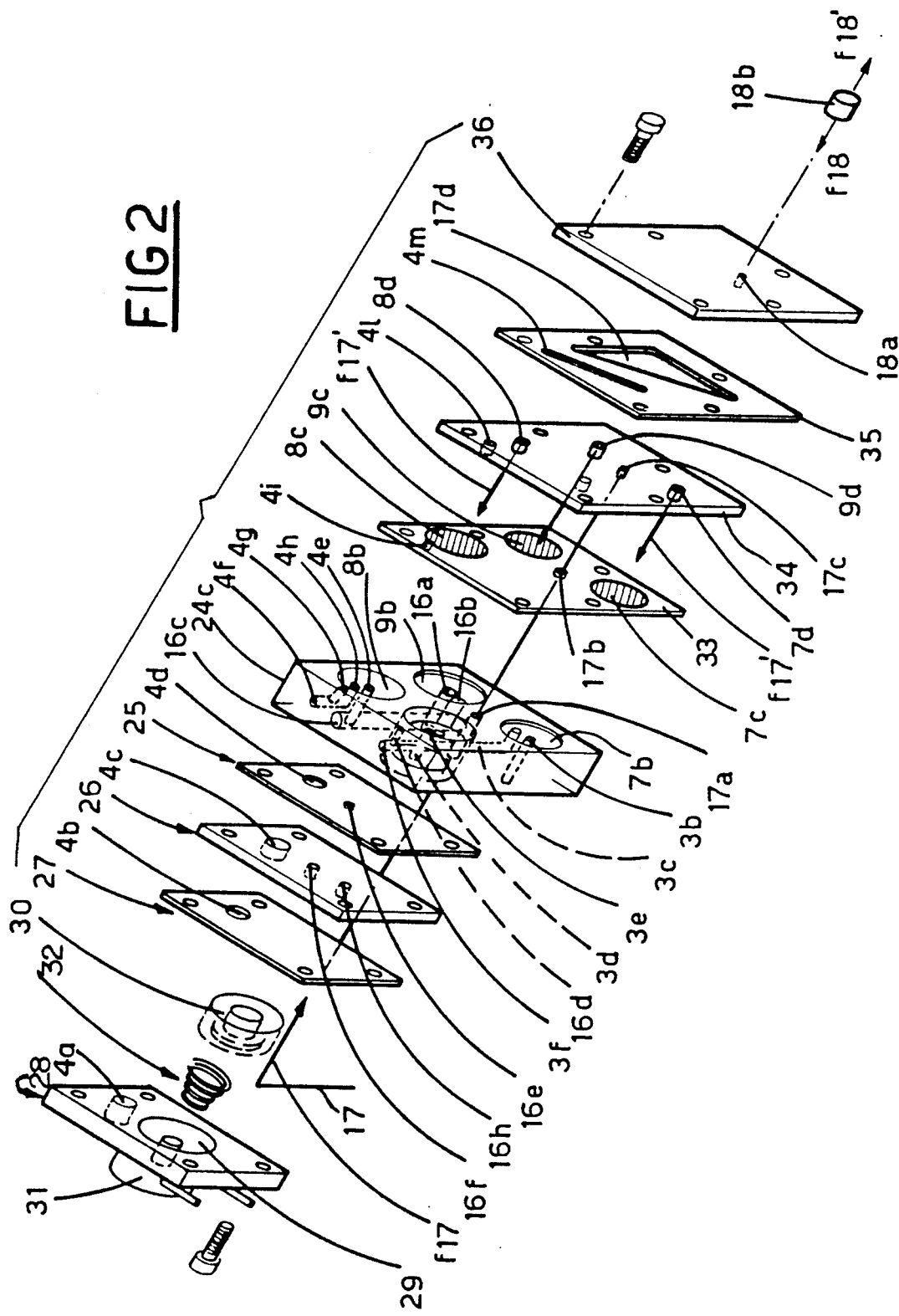

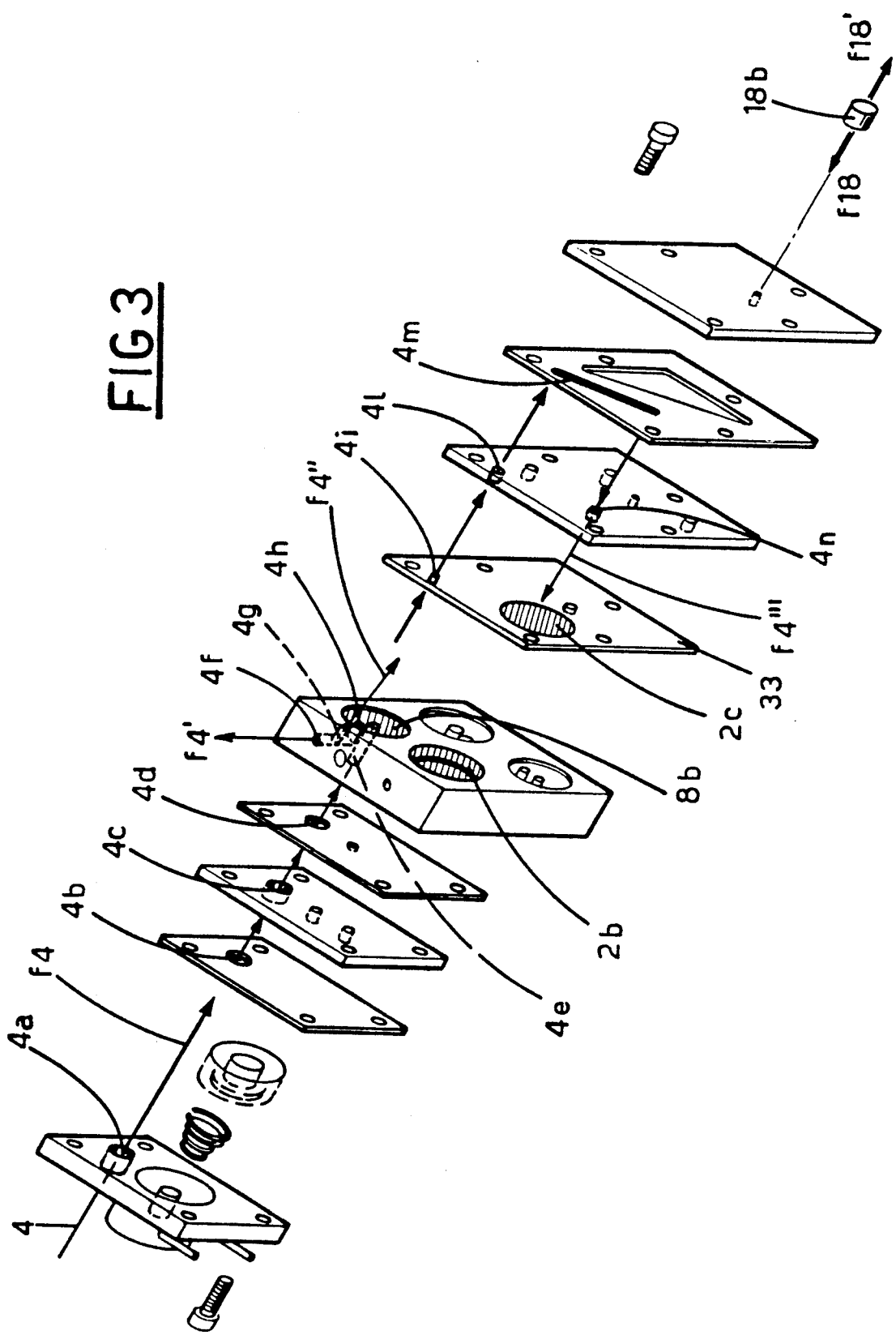

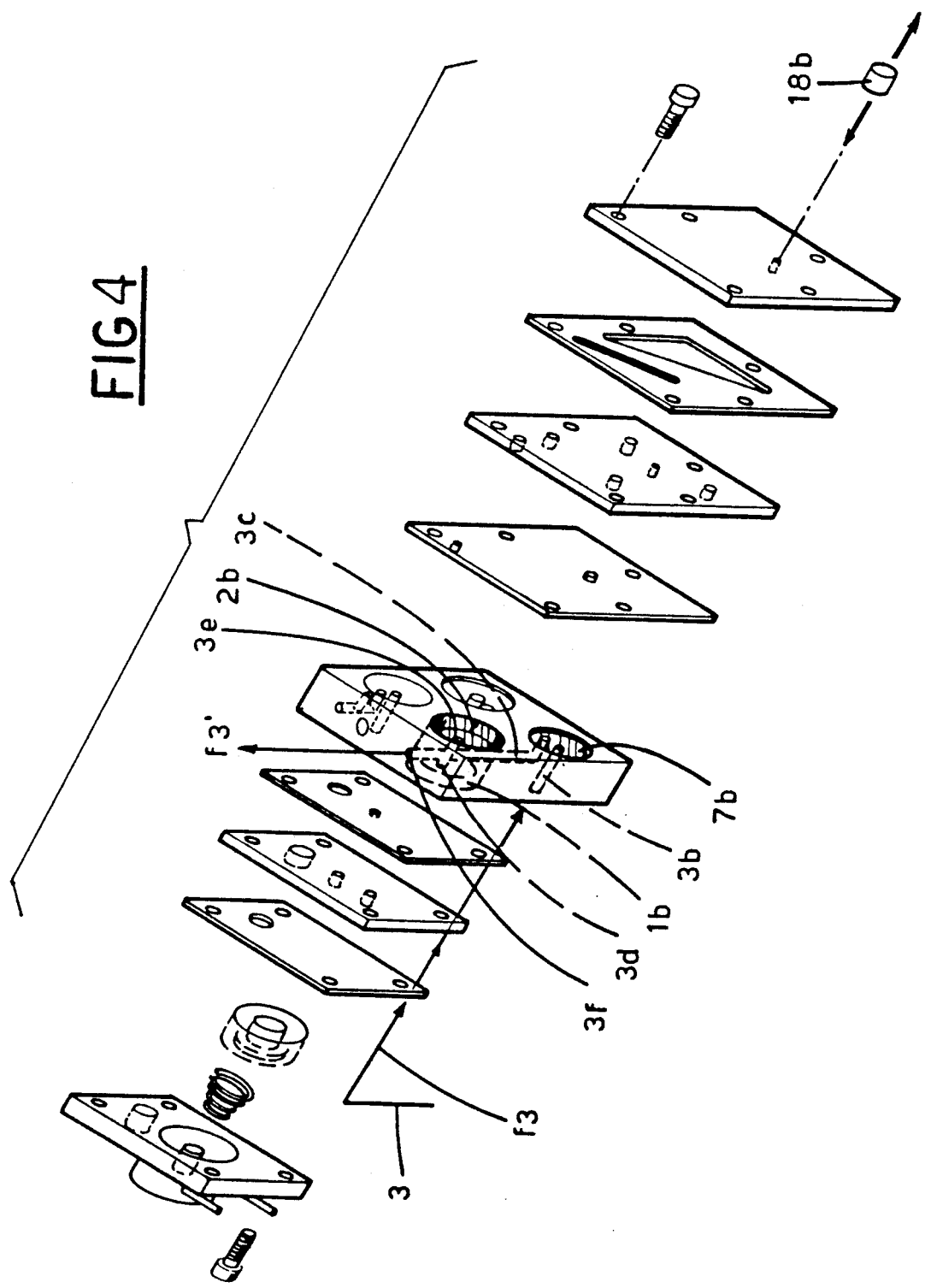

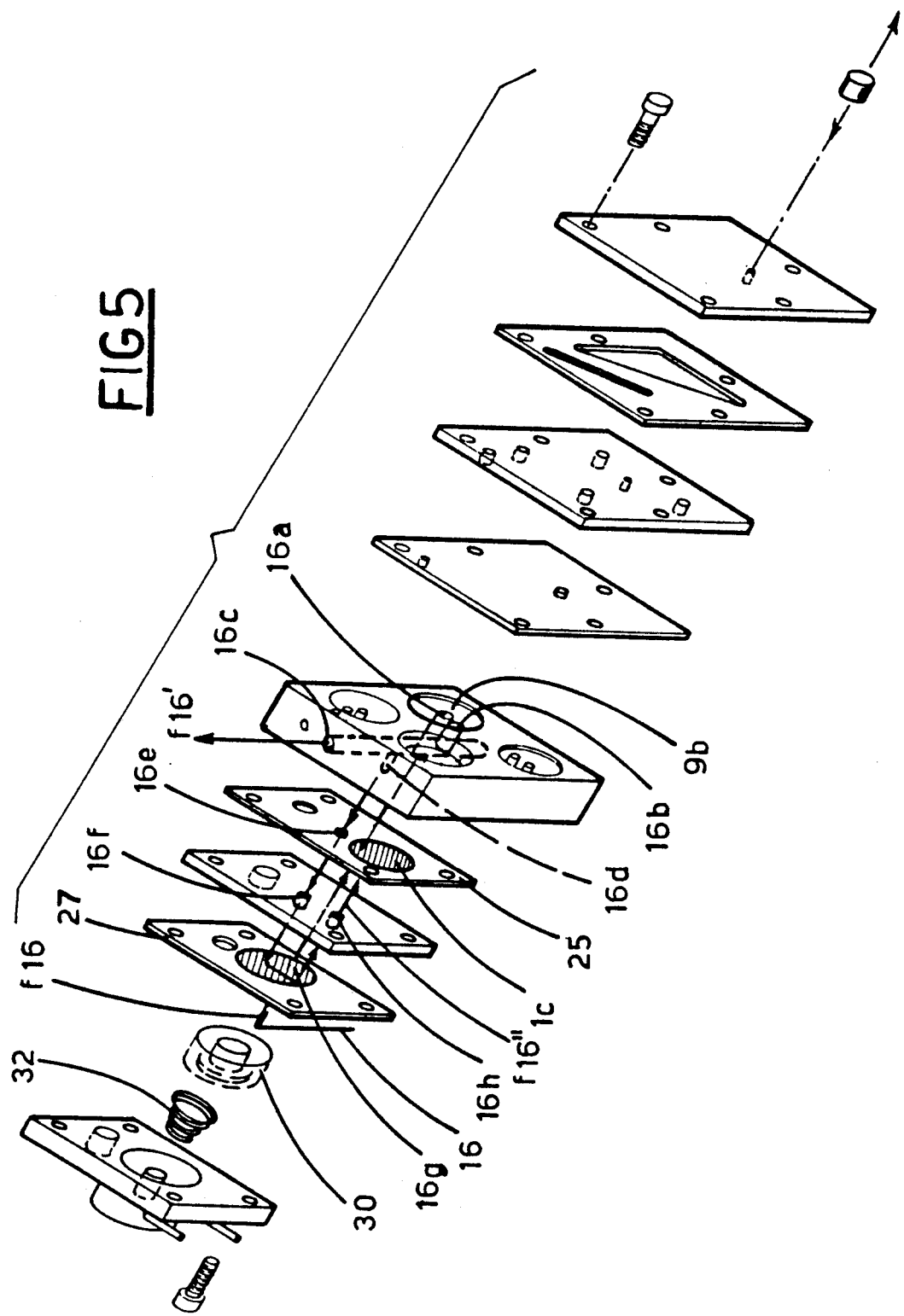

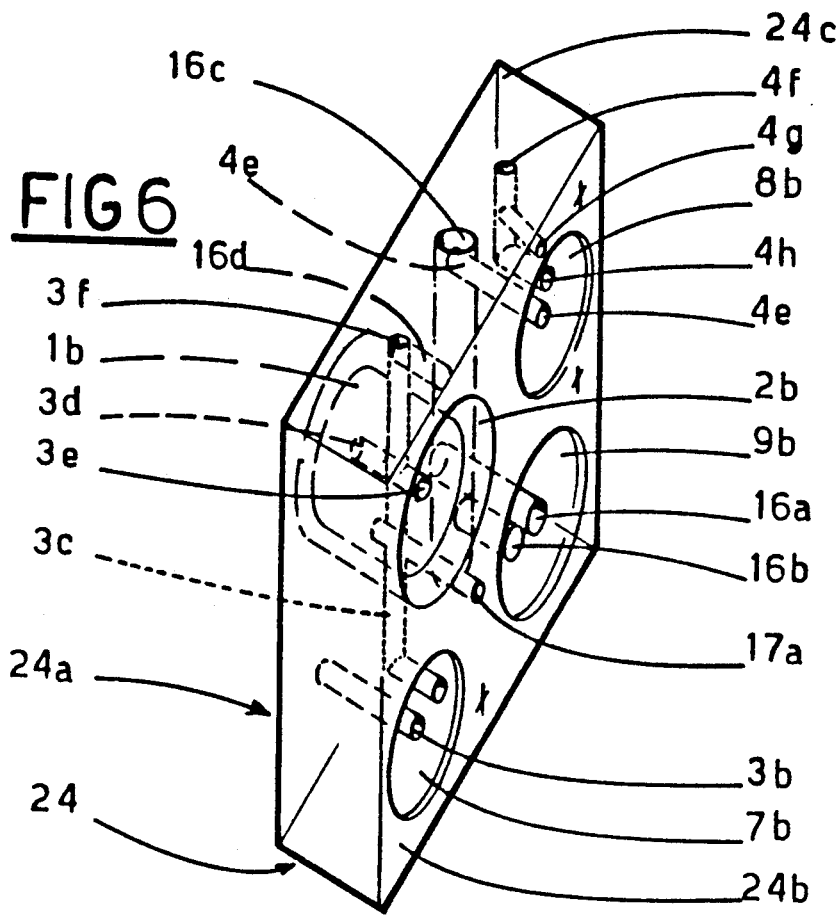

DRIP PREVENTING DEVICE FOR DENTAL INSTRUMENTS

BACKGROUND OF THE INVENTION

The present invention relates to a device that is designed to prevent dental surgery instruments and accessories from dripping at the moment when they are switched off.

In the art field of dental surgery instruments and accessories, and of their hygiene and improvement in particular, attempts have been made to render operation more efficient and effective by adopting devices and/or systems that prevent handpieces from dripping at the moment when they are switched off. More exactly, a great number of power driven dental surgery instruments utilize a water spray for the purposes of cooling and flooding the treatment area. This is particularly true in the case of high speed drills, which incorporate a pair of air and water circuits that produce an atomized spray.

Where no such system is provided, water will tend to drip from the instrument immediately following switch-off, in an annoying and unacceptable manner. The drip-inhibiting devices currently incorporated into dental surgery equipment make use of a plenum connected to the air and water circuits of the spray facility.

Air pressure being greater than water pressure in the circuits in question, the plenum is connected with spring means designed to operate such that when a given instrument is switched on initially (effected automatically when the user lifts the instrument from its holder), the plenum charges, in readiness to perform its prescribed function at the moment when the instrument ceases operation.

More exactly, with the spring means no longer under pressure, the plenum is able to generate a degree of vacuum, and thus to draw back water occupying the circuit downstream of the plenum and in the branches to the various instrument handpieces. Conventionally, the plenum is located upstream of the entire set of instruments, so that the need arises for a unit of generous capacity, capable of handling pressure requirements for any and all of the instruments installed.

The use of a large capacity plenum is also dictated by the length of the downstream circuit, hence the considerable pressure losses that must be offset. Another reason for installing a large unit is that one must often anticipate the future use of new and/or different instruments with increased circuit capacities.

A first drawback with the single plenum system is that the smaller capacity, or shorter branches of the circuit will be subjected to an overabundant negative pressure, causing water to be drawn back a considerable distance from the handpiece outlet. Such a situation is totally unhygienic, inasmuch as water that may have become polluted in and around the handpiece outlet is drawn back too great a distance into the circuit, together with air which may also be polluted.

Knowing the rapidity with which germs are able to multiply in such an environment, and their ability to gain the internal parts of the main equipment circuit, it will be clear enough that hygiene is lacking in a system of this conventional type. Accordingly, the object of the present invention is to overcome the drawbacks described above.

SUMMARY OF THE INVENTION

The stated object is realized by adoption of a drip prevention device as recited in the claims appended hereto; such a device is of the type incorporating a plenum connected with the water and air circuits of the spray system, which is designed to generate suction through the water circuit at the moment when an instrument or accessory is switched off.

According to the invention, use is made of at least one plenum for each instrument or accessory that uses water, located downstream of the valves by which the instruments or accessories are switched on and off and connected in addition to the power air circuit.

A first advantage provided by a device according to the invention is essentially that of its safe and faultless operation, ensured by the adoption of one plenum per single instrument, and by the reduced capacity of each circuit between the plenum and the outlet of the instrument handpiece; in the device disclosed, in fact, each plenum chamber can be matched in size to the amount of water that must be displaced through the particular handpiece.

A further advantage of the invention is that the instruments remain permanently primed for immediate use, as water is drawn back by suction through a minimal distance necessary to prevent dripping, rather than returning through an excessively long stretch of the circuit; accordingly, water will emerge immediately, atomized or otherwise, when the instrument is next switched on.

Another advantage of the invention is that the size of the single plenum serving one instrument remains unaffected by the addition of further instruments to the system, since every handpiece or accessory will be served by an indepenendent plenum of size to suit the capacity of its fluid outlet lines.

Yet another advantage of the invention is that of improved hygiene, ensured by virtue of the fact that the return of water from the instrument outlet is genuinely minimal, and at all events, limited to the handpiece.

BRIEF DESCRIPTION OF THE DRAWINGS

The invention will now be described in detail, by way of example, with the aid of the accompanying drawings, in which:

FIGS. 2 . . . 5 show a series of exploded perspectives illustrating the embodiment of a detail of FIG. 1 that forms part of each circuit connecting with a single instrument;

FIG. 6 shows a detail of FIG. 3 in enlarged scale, and more exactly, the housing in which the plenum chambers are located.

DESCRIPTION OF THE PREFERRED EMBODIMENTS

Figure 1:
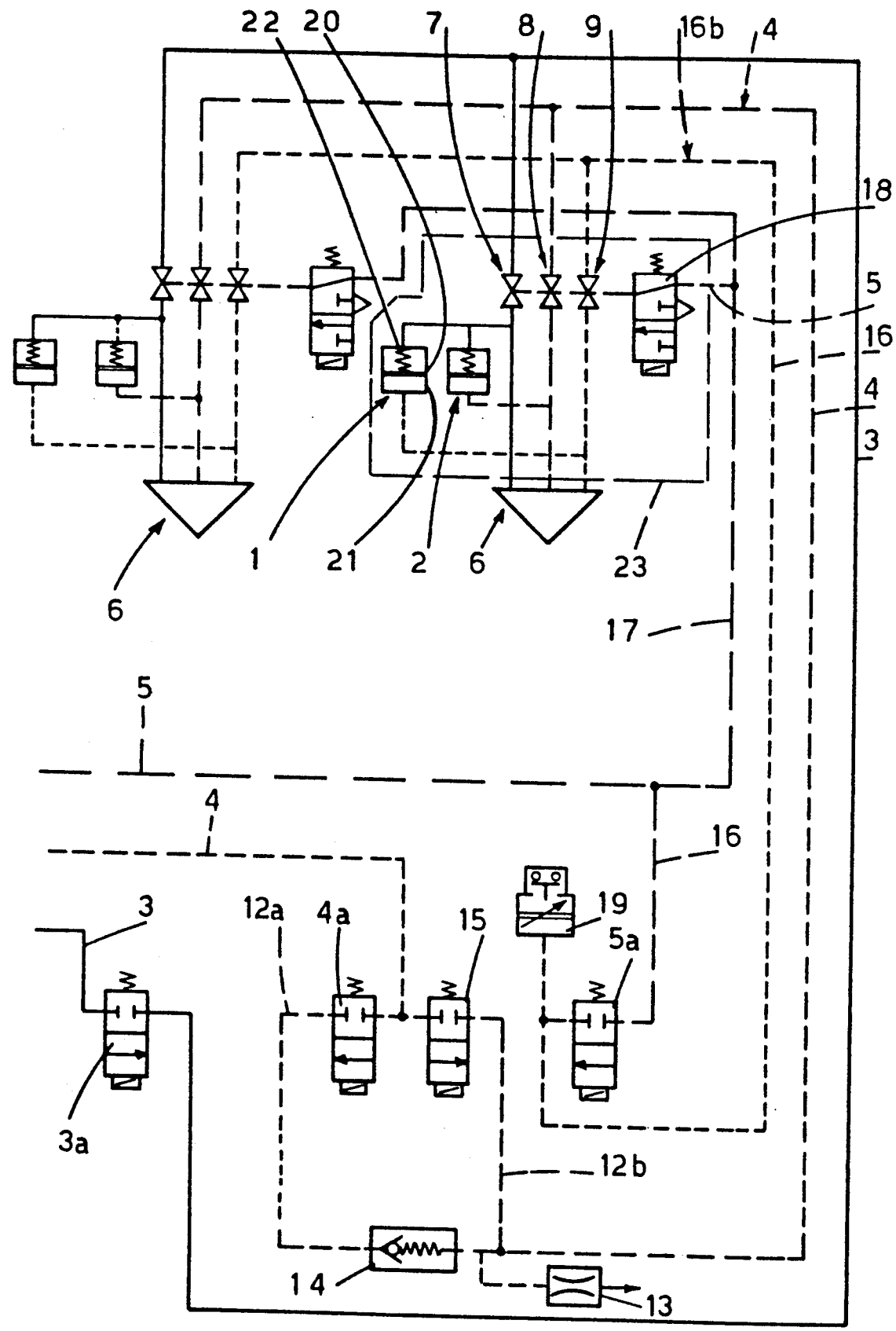
FIG. 1 is a circuit diagram of the complete fluid supply circuits for two dental surgery instruments, which incorporates the device disclosed, seen in a preferred embodiment.

With reference to FIGS. 1 and 2, the dental surgery equipment with which the instruments or accessories are associated comprises a water circuit 3, a spray air circuit 4, and a power air circuit 5; the two instrument handpieces are denoted 6.

The water circuit 3 is connected with the single handpieces 6 by way of a main shut-off valve 3a that governs all the instruments (generally a pedal operated type controlled by the dental surgeon during treatment), and individual on-off valves 7 associated one with each instrument 6 (operated to open automatically when the handpiece is removed from its holder).

Similarly, the spray and power air circuits 4 and 5 connect with the instruments 6 by way of a relative main shut-off valve 4a and 5a, and thereafter by way of individual on-off valves 8 and 9 associated with each handpiece 6.

The spray air circuit 4 is split through a certain stretch into two parallel branches 12a and 12b, one such branch 12a incorporating the main shut-off valve 4a, a check valve 14 and a restriction 13, installed in series along the flow-path of the air; the remaining branch 12b incorporates a chip-air valve 15, the purpose of which is to supply air to the handpiece 6 separately, with or without the instrument in operation. The check valve 14 enables air to be directed downstream of the two branches 12a and 12b when the chip-air valve 15 is opened, without passing through the spray branch 12a.

The power air circuit 5 is also split into two branches 16 and 17, the first of which connecting by way of the main shut-off valve 5a with the individual on-off valves 9 of the handpieces 6, and the second connecting directly with the valves 18, generally pneumatic (though solenoid operated types are also utilized), by which the on-off valves 7, 8 and 9 are controlled.

The first branch 16 of the power circuit 5 may also incorporate a pressure switch 19 enabling operation of the instrument on air only for safety reasons. With the second branch 17 connected directly to the single control valves 18, these will duly operate (when a handpiece 6 is removed from its holder) to open the on-off valves 7, 8 and 9 of the relative instrument in readiness for use, i.e. in receipt of air from the power circuit, and/or of air and water from the spray circuits.

As a general rule, the main shut-off valves 3a, 4a and 5a of the three circuits 3, 4 and 5 will be operated together by depressing a pedal, in such a way that the selected instrument 6 can be powered, and supplied simultaneously with atomized water and air from the spray circuits 3 and 4.

According to the invention, the conventional system described above is enhanced by the addition of at least one plenum chamber 1 for each instrument 6, located immediately upstream of the handpiece. In FIG. 1, which details the full circuitry for one instrument 6 only, given that the same system is duplicated for the other, two plenums 1 and 2 are installed between each handpiece and the relative on-off valves 7, 8 and 9.

Each plenum 1 and 2 is shown schematically in FIG. 1 as a spring-loaded piston 20, axially slidably in a barrel 21 connected to the water circuit 3 at one end, and at the other, to the power circuit 5 and the spray air circuit 4, respectively; 22 denotes the spring.

Needless to say, the end of the plenum 1 and 2 in communication with the air circuit 5 and 4 is that which diminishes in volume under the force of the spring 22.

A first, immediately discernible advantage of such an expedient is the facility it affords of constant drip prevention, even with the instrument 6 in receipt of power or chip air only.

With the plenum 1 and 2 located in close proximity to the relative instrument 6, and the intervening connection devoid of any obstructive components, or at any rate, of elements liable to induce pressure loss, calculation of the size of the plenum 1 and 2 can be rendered extremely precise, as also can the distance through which the water returns back into the circuit 3; in short, it becomes possible, at very least, to control suction so that the water will return to a point just short of the handpiece outlet.

FIGS. 2, 3, 4 and 5 illustrate a possible embodiment of the assembly of components grouped together in the envelope denoted 23 in FIG. 1, namely, the three on-off valves 7, 8 and 9 and the plenum chambers 1 and 2.

The four figures differ from one another inasmuch as the bold line denotes the fluid circuit rendered operative in each instance.

The three valves 7, 8 and 9 and the two plenum chambers 1 and 2 are combined in one substantially flat, square housing 24 (see also FIG. 6), of which one face 24a exhibits a chamber denoted 1b, and the opposite face 24b exhibits four chambers 2b, 7b, 8b and 9b located adjacent to the four corners. The chambers denoted 1b and 2b are positioned in mutual alignment on either side of a plane lying between and parallel with the two relative faces 24a and 24b of the housing, and interconnected by way of a hole divided into two stages 3d and 3e (connecting with chambers 1b and 2b respectively) by a longitudinal passage 3c, of which one end 3f emerges at the top 24c of the housing, as viewed in FIG. 6, and the remaining end bends toward the face denoted 24b and emerges into the chamber 7b below, which, it will be observed, connects with the opposite face 24a of the housing 24 by way of a further hole 3b.

The chamber denoted 8b connects directly with the opposite face 24a of the housing 24, via a through hole 4e, as well as affording a passage 4h in three stages, of which a second stage 4f connects with the top 24c, and a third stage 4g with the face 24b of the housing occupied by the chamber 8b itself. The chamber denoted 9b exhibits a hole 16a which connects with the opposite face 24a of the housing, and a passage denoted 16b that connects with the top 24c of the housing via a first additonal stage denoted 16c, and with the opposite face 24a by way of a second additional stage 16d.

Lastly, 17a denotes a hole passing straight through the housing 24 and interconnecting the two faces 24a and 24b.

Associated with the one face 24a of the housing, one has a first flexible fluid-tight diaphragm 25, a first plate 26, a second flexible fluid-tight diaphragm 27 and a second plate, or cover 28, which are fitted in the sequence thus recited. The two diaphragms 25 and 27 and the two plates 26 and 28 are of identical size and shape, totally masking the relative face 24a of the housing 24, except for the three holes 3b, 16a and 17a, and embodied with relative through holes 4d, 4c, 4b and 4a all of which align coaxially with the hole in the housing denoted 4e.

The first diaphragm 25 and first plate 26 also exhibit respective holes 16e and 16f located in coaxial alignment with the hole denoted 16d, and similarly, the first and second plates 26 and 28 exhibit respective holes 16h and 29 aligned with the chamber 1b first mentioned.

The hole 29 in the second plate 28 affords the seat for an annular piston 30, which is retained by a cover 31 and biased toward the second diaphragm 27 by a spring 32 located between piston and cover, thereby creating a pneumatically operated safety switch that enables operation of the instrument (or enables a given function of the instrument) with compressed air only, at a given pressure (triggered by an electrical contact not illustrated in the drawings).

Associated similarly with the opposite face 24b of the housing 24 are a third flexible fluid-tight diaphragm 33, and a third, a fourth and a fifth plate 34, 35 and 36, all exhibiting dimensions such as ensure that the relative face 24b of the housing is entirely masked.

The third diaphragm 33 and the third plate 34 each exhibit two holes 4i, 17b and 4l, 17c respectively, located in coaxial alignment with the holes in the housing denoted 4g and 17a, respectively; also, the third plate 34 exhibits four additional holes 4n, 7d, 8d and 9d, coinciding respectively with the four chambers 2b, 7b, 8b and 9b of the housing 24. The fourth plate 35 (a diaphragm in most instances, to all intents and purposes) presents two ports 4m and 17d, of which the first coincides with the holes of the third plate 34 denoted 4l and 4n, and the second with those denoted 17c, 7d, 8d and 9d; with the diaphragms and plates assembled and fitted to the face of the housing 24, the ports 4m and 17d afford further chambers, as will become clear in due course.

The fifth plate 36, which provides the outer cover, incorporates a vent hole 18a positioned to coincide with the second port 17d in the fourth plate 35; 18b denotes a sliding plunger by which the vent 18a is blocked and opened.

As regards operation of the equipment, simultaneous reference is made to FIG. 1, and FIGS. 2 . . . 5. Internally of the envelope 23 of FIG. 1, the water circuit passes through holes 3b, 3c, 3d, 3e and 3f; accordingly, the circuit denoted 3 can be traced in FIGS. 2 . . . 5 through the various passages referred to with the number 3.

The same principle is applied for the air circuits 4, 16 and 17 and the on-off valves 7, 8 and 9.

Operation of the device will now be described with reference to the various drawings, starting from the situation in which all instruments 6 are in the at rest condition, namely, with the handpiece in its holder in conventional manner, pressing against the plunger 18b and blocking the vent 18a in the housing cover (see arrow f18 in FIG. 2).

In this situation, the continuously pressurized branch 17 of the power air circuit 5 directs air through holes 17a, 17b and 17c (arrow f17, FIG. 2) into the relative port 17d, thence through holes 7d, 8d and 9d and against the third diaphragm 33, impinging on the areas denoted 7c, 8c and 9c (which are cross-hatched in FIG. 2). Thus, the diaphragm 33 is pushed into the corresponding chambers 7b, 8b and 9b of the housing 24 to the point of blocking holes 3b and 3c, 4e and 4h, and 16a and 16b; in short, the three on-off valves 7, 8 and 9 are held in the closed, 'off' position (arrow f17', FIG. 2). Removing a given handpiece from its holder at this point to operate the relative instrument 6, the plunger 18b will shift (arrow f18', FIG. 2), forced back by the pressure of air in the second port 17d, and if installed, by a spring (not illustrated). With the plunger thus released, and air allowed to exhaust from the port 17d through the vent 18a, the diaphragm 33 can return to its at-rest position, opening the three on-off valves 7, 8 and 9. The on-off valves 7, 8 and 9 receive neither air nor water as yet, despite being in the 'on' state, as the main shut off valves 3a, 4a-15 and 5a are still closed upstream; thus, one has a "stand-by" condition in which the instrument 6 is operational, though not ultimately switched on.

Accordingly, the next step is that of switching on the instrument, i.e. of opening up the shut-off valve 5a controlling admission of air through the first branch 16 of the power circuit 5 (arrow f16, FIG. 5) and into the bottom part of the housing 24; from here, air passes through the hole 16a in the relative chamber 9b, which is no longer blocked by the third diaphragm 33, and into passages 16b, 16c, 16d, 16e and 16f, reaching the handpiece 6 by way of 16c. Air emerging through the first hole 16f in the first plate 26 impinges on the area of the second diaphragm 27 denoted 16g, forcing the piston 30 back against its spring 32, and returns via the second hole 16h to strike the first diaphragm 25 at 1c and urge it fully into contact with the internal surfaces of the relative chamber 1b (arrow f16", FIG. 5). When the instrument 6 is switched off subsequently, i.e. when the shut-off valve 5a is returned to the closed position, pressure will be removed from the hole 16h in question, enabling the diaphragm 25 to regain its former at-rest position, distanced from the surfaces of the chamber, whether flexing naturally and/or returned by a spring.

Given that the first diaphragm 25 creates a fluid-tight seal with the face 24a of the housing 24, and that one hole 3d only affords a possible exit from the relative chamber 1b, the return of the first diaphragm 25 to its at rest position generates a degree of negative pressure through the connecting water-filled passages 3b, 3d, 3e and 3f, causing the water to be drawn back from the handpiece 6 by an amount equivalent to the displacement of the chamber 1b (see FIG. 6).

With the spray circuits 3 and 4 also activated by the opening movement of the relative main shut-off valves 3a and 4a, water is caused to flow through hole 3b (arrow f3, FIG. 4), chamber 7b and passages 3c, 3d and 3e, thence out to the handpiece 6 by way of the top hole 3f (arrow f3', FIG. 4), and into the chambers 1b and 2b of the first plenum 1 and the second plenum 2 by way of 3d and 3e.

At the same time, spray air is directed through holes 4a, 4b, 4c, 4d and 4e (arrow f4, FIG. 3) into the chamber denoted 8b and out to the handpiece 6 by way of the connected passage 4h-4f (arrow f4', FIG. 3); the same air also reaches the first port 4m of the fourth plate 35, passing through 4g, 4i and 4l (arrow f4").

Spray air in the first port 4m is thus able to find its way through the hole denoted 4n and impinge on the third diaphragm 33 at 2c (arrow f4''', FIG. 3), with the result that the diaphragm is urged toward the housing 24 and into full contact with the walls of the relative chamber 2b. When the circuit is switched off subsequently, air pressure inside the port 4m and the connecting hole 4n will drop, and accordingly, the diaphragm 33 is able to return to its at-rest position, generating negative pressure in the chamber 2b in similar fashion to the first diaphragm 25 and causing water to be drawn back from the handpiece toward the relative passage 3f. Replacing the handpiece 6 in its holder, the vent hole 18a is once again blocked by the plunger 18b, whereupon pressure rises in the port 17d and the on-off valves 7, 8 and 9 are returned to the closed position.

Given that the distance between the passages 3f, 4f and 16c of the housing 24 and the outlet of the handpiece is thus limited, and that the dimensions of the interconnecting passages remain unaltered (it will be observed that there are no valves or other intervening components of variable section), the displacement of the chamber 1b and 2b of each plenum 1 and 2 can be calculated with considerable precision, in order to avoid too high a negative pressure, hence an excessive force of suction, in the relative branch of the circuit that connects with the instrument 6.

The limited distance between the housing 24 and the handpiece 6 also ensures a marked speed of response when switching on the instrument, as the water need cover only a short distance in reaching the outlet of the handpiece; what is more, the adoption of the twin plenum arrangement illustrated further ensures that no water will drip from the handpiece, even when operated dry (power air only) or used to blast away debris (chip-air only).

What is claim:

1. A device serving to prevent dental surgery instruments and accessories from dripping water at the moment of switch-off, comprising at least one plenum for each instrument, connected to relative water and air circuits at a point immediately upstream of the instrument and charged with air, received under pressure from the relative circuit at the moment when the instrument is switched on, in such a way as to generate negative pressure through the water circuit when the instrument is subsequently switched off.

2. A device as in claim 1, wherein each plenum is located downstream of the on-off valves controlling the branches of the water circuit, a spray air circuit and a power air circuit that connect with the relative instrument.

3. A device as in claim 1, comprising two plenums for each instrument, installed in parallel, each of which is connected at one end to the water circuit, wherein the remaining end of the one plenum is connected to the spray air circuit, and the remaining end of the other connected to the power air circuit.

4. A device as in claim 2, comprising pneumatically-operated on-off valves incorporated into a single housing directly associated with each instrument, wherein the plenum is similarly incorporated into the housing and connected to the water and air circuits.

5. A device serving to prevent a plurality of dental surgery instruments and accessories from dripping water at the moment of switch-off, comprising a plurality of plenums with at least one plenum for each instrument, connected to relative water and air circuits at a point immediately upstream of the instrument and charged with air, received under pressure from the relative circuit at the moment when the instrument is switched on, in such a way as to generate negative pressure through the water circuit when the instrument is subsequently switched off.

6. A device as in claim 5, wherein each plenum is located downstream of the on-off valves controlling the branches of the water circuit, a spray air circuit and a power air circuit that connect with the relative instrument.

* * * * *